United States Patent [19]

Zucker et al.

[11] 4,333,611
[45] Jun. 8, 1982

[54] PROCESS FOR DECOMPOSING CELLS OF BIOMASSES OR THE LIKE

[75] Inventors: Friedrich J. Zucker, St. Andreasstrasse 16, D-4040 Neuss 21, Fed. Rep. of Germany; Georg Osthaus, Neuss, Fed. Rep. of Germany; Doris Zucker-Kerbler, Vienna, Austria

[73] Assignee: Friedrich Josef Zucker, Neuss, Fed. Rep. of Germany

[21] Appl. No.: 145,915

[22] Filed: May 2, 1980

[30] Foreign Application Priority Data

May 5, 1979 [DE] Fed. Rep. of Germany ....... 2918212

[51] Int. Cl.³ .............................................. B02C 19/00
[52] U.S. Cl. ........................................ 241/1; 241/2; 241/23; 432/13
[58] Field of Search ................... 241/1, 2, 23; 432/13

[56] References Cited

U.S. PATENT DOCUMENTS 2,873,220  2/1959  Brownell et al. .................. 241/2 X
4,084,757  4/1978  Rakitin et al. ....................... 241/1 X Primary Examiner—James M. Meister
Attorney, Agent, or Firm—John C. Smith, Jr.

[57] ABSTRACT

The decomposition of cells of biomasses or the like or of substrates containing biomass, e.g. for releasing cell content substances, for separating cell content and cell sheath or for inactivating enzymes or the like is performed by heating and expanding. According to the invention, the biomass or the like is heated by friction, optionally under pressure, to temperatures above the point of evaporation of water and it is subsequently expanded into atmosphere or in a reduced pressure. As for the apparatus, the cells of biomasses or the like are decomposed by means of a centrifugal machine in which a rotor and a stator with facing radial surfaces are coacting. Between the rotor and the stator, there is provided a gap producing frictional heat in a predetermined amount for the material passed continuously therethrough, and at the outlet of the gap, there is an expansion chamber which is in communication the atmosphere.

7 Claims, 2 Drawing Figures

PROCESS FOR DECOMPOSING CELLS OF BIOMASSES OR THE LIKE

The invention relates to a process and an apparatus for decomposing cells of biomasses or of substrates containing biomasses, e.g. for releasing cell content substances, for separating cell content and sheath and for inactivating enzymes or the like.

Cells in aggregations and in a single form, e.g. microorganisms, cell cultures or the like have to be treated in many technical procedures. Generally, two aims are pursued. On the one hand, the cell shall be desintegrated to release the content substances or to separate the content from the sheath. On the other hand, microorganisms and spores shall be killed by heating and/or desintegration, and enzymes shall be inactivated accordingly.

It has been known to decompose cells by mechanical stress, e.g. by ball mills, high pressure homogenizers. The attempt had been also made to effect decomposition by expansion, e.g. with the French press. Moreover, a sterilization is effected by heating and expansion, e.g. with the uperisation of milk, comprising heating by vapor. The known decomposing methods are still imperfect. In the case of the mechanical method, mechanical wear of the apparatus is high. In the case of a decomposition by expansion, the process can be dominated but very badly, so that for instance the French press method is not suitable for industrial use. In the case of the indirect heating under vapor injection through nozzles, the energy yields are worse.

It is the object of the invention, to decompose cells of biomasses or of substrates containing biomass by heating and expanding by mechanical means in a quick and careful manner and with a high yield. The invention is characterized in that the biomass, optionally under pressure, is heated by friction at temperatures above the evaporation point of water, and that it is subsequently expanded into atmosphere or in a reduced pressure.

By heating by friction the material without a substantial pressure, cells are caused to burst in the largest sense. If the temperatures caused by frictional heat are as high as about 120° to 130° C. and even higher and if the material is then expanded, the contents of the cells are released for many different purposes. No heat transition problems do exist by the friction, and the resulting energy yield is maximum. The use of friction permits tempering within a very short time. Thus, a thermal stress of the biomass or of the material to be sterilized is avoided to a great extent. This treatment is very suitable if no direct vapor is allowed. The outputs of the decomposition are very high and the mechanical wear is very low.

The method of treatment according to the invention is preferably suited for biomasses having a high percentage of dry substances. It may be so high that the biomass is just still pumpable, if e.g. a high pressure homogenizer will fail due to lack of mobility of the mass or where a dilution will take place by vapor injection.

According to another feature of the invention, the apparatus for decomposing cells of biomasses or the like by frictional heat is characterized in that with the use of a centrifugal machine in which a rotor and a stator having facing radial surfaces is cooperating, there are provided between the rotor and the stator a gap producing frictional heat in a predetermined amount for the continuously flowing material and an expansion chamber at the outlet cross section of the gap, which chamber is at atmospheric or lower pressure.

With such an apparatus, the material may be suddenly heated to the temperature of water evaporation and higher by the friction between rotor and stator. The operation takes place within a fraction of a second. At the end of the path through the rotor-stator-gap, there is an expansion into atmosphere or into a vacuum, thus causing the vapor-filled cells being also under an internal pressure to burst with a possibly simultaneous mechanical stress. This operation taking only fractions of seconds, the thermal load for the material is only very slight. The resulting treatment of the material is careful and the efficiency is very high. At the same time, when the cells are bursting, the decomposed cells or the material to be sterilized may be cooled by water evaporation and/or evaporative cooling.

It is advantageous to provide between the rotor and stator such a gap that its walls relative to its outlet cross section—seen in cross section—extend at an acute angle. However, the walls of the gap may also extend in parallel relative to each other. The most narrow gap cross section is generally in the range from 2 $\mu$m to 200 $\mu$m, subject to the type of the material. The speed of the rotor may be kept preferably between 500 rpm to 3000 rpm. The distance between the gap walls in axial direction should be suitably changeable. To this effect, the stator is adjusted and the displacement of the stator relative to the change of the gap may be controlled subject to the temperature of the material at the outlet cross section.

The wall faces of the rotor and of the stator facing the gap are preferably rough. This may be realised for instance by a corresponding metal alloy. Moreover, a baffle surface extending partly or totally roundabout may be provided at a distance from the outlet cross section of the annular gap so that the material will get from the baffle surface to the expansion chamber of a correspondingly great dimension. Thus, it is also possible to better separate from the cell components the vapor discharged from the cells and to easily lead it away.

The apparatus may be so designed that a passage for the material is provided at both sides of the rotor plate. Generally, the inlet cross section of the gap will be provided at the small diameter of the rotor so that the material will flow from the inside to the outside. However, the inlet cross section of the gap may be also at the outer diameter of the rotor. In such a case, the material is urged from the outside to the inside against the natural direction of conveyance of the apparatus.

The invention will be now explained by means of embodiments shown in the enclosed drawing.

Figure 1:
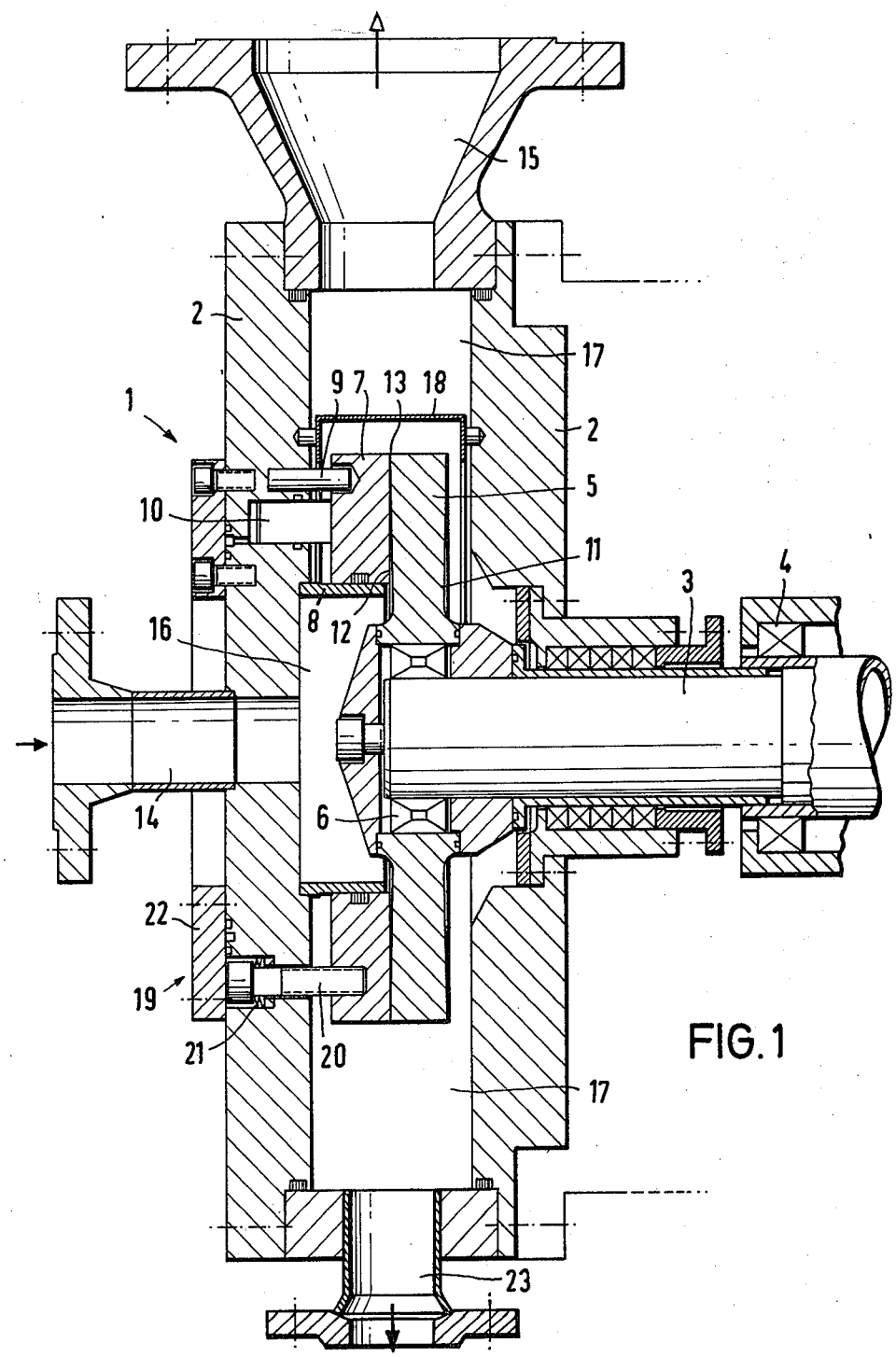
FIG. 1 shows a sectional and schematic view of an embodiment of an apparatus for decomposing cells of biomass.

The apparatus 1 for decomposing the cells of biomasses etc. has a housing 2 in which a shaft 3 is mounted rotatably by means of bearings 4 and can be driven by a (non-illustrated) drive, e.g. an electric motor. At the free end of shaft 3, a rotor 5 in the form of a plate is rotatingly mounted integrally with the shaft via clamping ring elements 6. The rotor plate 5 faces a stator plate 7 carried by bushing 8 and protected against rotation by pins 9. Between the rotor 5 and the stator 7, there is a gap 11 whose entry cross section at 12 is larger than the outlet cross section 13 at the outer diameter of rotor and stator. 14 designates the inlet or entry, 15 designates the vacuum connection and 23 the outlet. The material is conducted through the inlet in the longitudinal axis of the apparatus to chamber 16. After having left gap 11, the material gets into the expansion chamber 17 which, as an annular chamber, has a considerable radial dimension, e.g. the radial dimension of the annular expansion chamber 17 may be equal to or greater than the radial length of gap 11. In a predetermined distance from the outlet cross section 13 of gap 11, there may be mounted a baffle plate 18 extending roundabout in part or as a whole. At the outlet 15, there may follow a vacuum unit through which the material can be quickly cooled.

The stator 7 may be mounted on the bushing 8 to be displaceable in axial direction. To this effect, an adjusting means 19 and 20 may be provided. The adjusting means may comprise for instance a hydraulic cylinder 10 and a resetting screw 20 with cup springs 21. The housing 2 is closed by a cover plate 22 at the side of the stator.

The opposite plane surfaces of rotor and stator are preferably rough. This may be realised by selecting a suitable metal alloy. The size of the gap 11 at the outlet end 13 may be set to about 0.01 mm or may be adjusted down accordingly. Due to the centrifugal force of the rotor and of the tapering gap between rotor and stator, the material is suddenly heated by friction to the temperature of water evaporation or even higher. Thereafter, an expansion takes place in chamber 17, and, as a result, the vapor-filled cells which are under internal pressure are caused to burst. Due to the high speed of shaft 3 and of rotor 5, the material is passing gap 11 only for fractions of seconds and for the intended purpose it is exposed only practically to a minimum thermal load. The total operation is taking place in a quick, continuous procedure.

Figure 2:
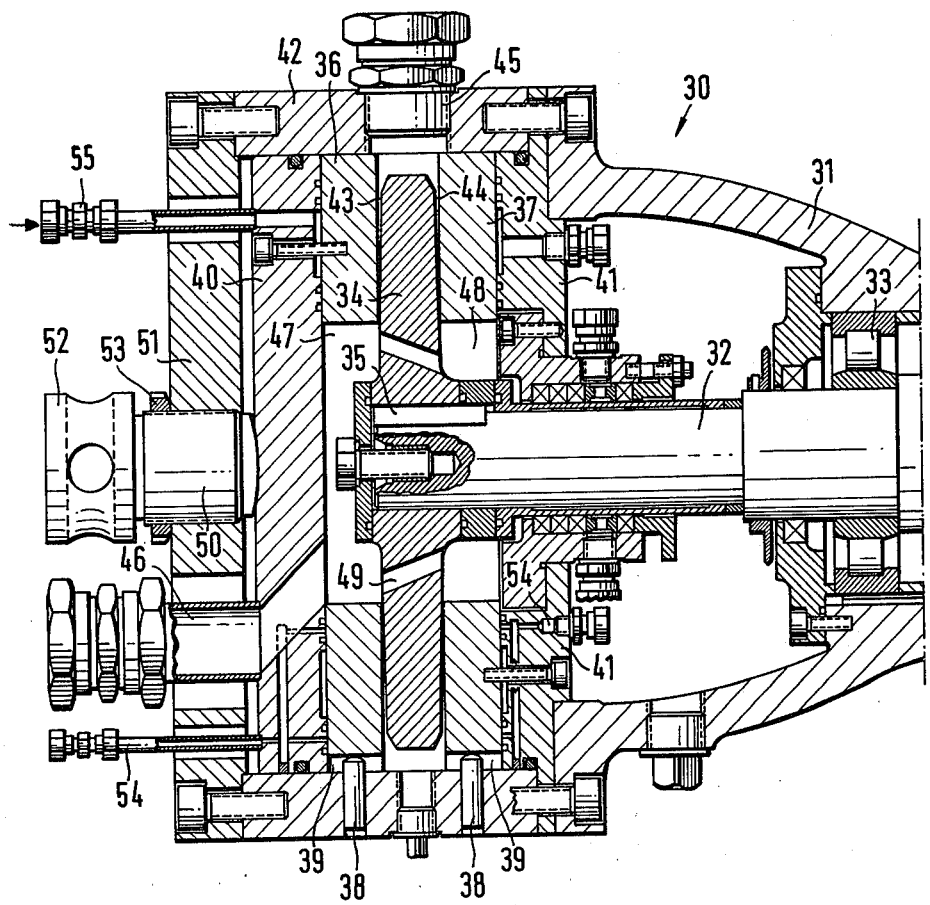
FIG. 2 illustrates schematically a sectional view of another embodiment of the apparatus in which the medium under treatment is positively passed against the natural conveyor device.

The apparatus 30 of FIG. 2 is so designed that the medium under treatment is passed positively against the natural conveyor direction. In the housing 31, there is supported rotatably by means of the roller bearing 33 the drive shaft 32. At its front end, it is provided with the rotor plate 34 which is rotatingly mounted to be integral with shaft 32 by means of wedge 35. At both sides of the rotor plate 34, there are the stator plates 36 and 37 which, by means of pins 38 engaging transverse grooves 39 of the annular plate 36 and 37 are protected against torsion. At both sides of the stator ring plates 36 and 37, there are provided housing plates 40 and 41. The housing plate 41 is provided to abut at the housing 31 while the housing plate 41 is supported to be displaceable within the housing jacket 42. The gap 43 and 44 between the rotor plate 34 and the two stator plates 36 and 37 have a larger inlet cross section at the outer diameter than at the inner diameter of the stator plates 36 and 37. 45 designates the inlet for the material and 46 is the outlet. At the inside of the stator plates 36 and 37, there is the expansion chamber 47 and 48 the interconnection being realised by means of bores 49.

A pressure bolt 50 is acting on the displaceable housing plate 40, the bolt being screwed into a cover plate 51 and it being adjustable manually by means of item 52. 53 designates a counter-nut. By means of the pressure bolt 50, the housing plate 40 is displaced towards the rotor plate 34 so that at the outlet cross section at the expansion chamber 48 the desired gap is adjusted at both sides. Through the inlet 55, the heat exchange medium may be supplied. Device 54 comprises a leakage protection for the O-ring seal.

In case of the device of FIG. 2, the material under treatment is fed under pressure through the inlet 45 at the outer periphery of the housing to the gaps 43 and 44 between rotor 34 and the two stators against the centrifugal force caused by the rotating rotor 34, whereafter the material passes through the outlet cross section of gaps 43 and 44 into the expansion chamber 47,48,49 and from there through the outlet 46. In this connection, the material is subjected to a still more intense friction with the object of somewhat extending the time of expansion.

Both devices may be operated with a thermally adjusted gap or with a throughput-controlled temperature.

The disclosed devices can be used for decomposing the cells of the medium for different purposes.

To decompose biomasses in order to release the cell content substances, the culture medium or washing fluid is removed to such an extent that e.g. a bacteria mass can be still pumped. It is heated in one of the described devices until the cells are bursting during the expansion. The temperature is dictated by the condition of the cell. By evaporative cooling, the material is cooled at the same time. Thus, cell content substances can be released and further processed in a very careful manner.

In the same way, cells may be decomposed with the object of releasing intracellular water to achieve a far-reaching, careful concentration or drying of biomasses.

Moreover, an intentional fermentation is possible by means of the devices. For instance for the production of fresh cheese, use is often made of mixed cultures of bacteria and the processing becomes more difficult accordingly. By the careful heating of the material by friction with a subsequent expansion and probably evaporative cooling, the operation may be performed as follows: fermentation with culture A, inactivation by friction, fermentation with culture B, etc., and, finally, sterilization by friction.

The disclosed devices lend themselves additionally to pasteurization or sterilization of products (e.g. fresh cheese preparations, recombined milk concentrates, cocoa or chocolate masses, fruit pulps, etc.) by heating by friction either with immediate expansion or with a residence time under pressure and later expansion in order to allow a longer action of temperature to inactivate enzymes and microorganisms.

Furthermore, a homogenization with pasteurization or sterilization of fruits may be carried out. Cells may be also decomposed prior to drying in order to expel water and residue water. By this means, a very careful drying procedure for bio-masses or the like may be achieved.

What is claimed is:

1. A process for decomposing cells of biomasses or the like or of substrates containing biomasses by heat and expansion, comprising passing said biomass through a gap between confronting surfaces of at least two elements, at least one of said elements moving with respect to the other of said elements at a sufficient speed and the width of said gap being sufficiently narrow to cause sudden heating of said biomass due to friction between said surfaces, and then directing said heated biomass from said gap into a chamber whereby the cells of said biomass are caused to burst due to the vapor generated in said cells by said heat.

2. The process of claim 1 wherein the cross-sectional width of said gap is between 2 μm and 200 μm.

3. The process of claim 2 wherein said confronting surfaces of said at least two elements are maintained at an acute angle with respect to each other.

4. The process of claim 2 or claim 3 wherein said elements having confronting surfaces defining said gap comprise a stator and a rotor respectively, the speed of said rotor being maintained between 500 rpm and 3000 rpm.

5. The process of claim 1 wherein said biomass is heated to at least a temperature at which water is caused to vaporize during its passage through said gap.

6. The process of claim 5 wherein a vacuum is maintained in said chamber to accelerate bursting of said vapor-filled cells.

7. The process of claim 1 wherein a continuous stream of said biomass flows through said gap and chamber.

* * * * *